US009173992B2

(12) United States Patent
Bengtsson et al.

(10) Patent No.: US 9,173,992 B2
(45) Date of Patent: Nov. 3, 2015

(54) SECURE PAIRING OF ELECTRONIC DEVICES USING DUAL MEANS OF COMMUNICATION

(75) Inventors: Henrik Bengtsson, Taastrup (DK); Jens Aage Munk, Ølstykke (DK); Nils Göran Marnfeldt, Höllviken (SE); Per Hvid Hansen, Lynge (DK); Per Einar Pontus Holm, Tygelsjö (SE); Terkel Valentin Thomsen, Helsinge (DK)

(73) Assignee: Novo Nordisk A/S, Bagsvaerd (DK)

( * ) Notice: Subject to any disclaimer, the term of this patent is extended or adjusted under 35 U.S.C. 154(b) by 240 days.

(21) Appl. No.: 12/282,576

(22) PCT Filed: Mar. 13, 2007

(86) PCT No.: PCT/EP2007/052336
§ 371 (c)(1),
(2), (4) Date: Nov. 4, 2008

(87) PCT Pub. No.: WO2007/104755
PCT Pub. Date: Sep. 20, 2007

(65) Prior Publication Data
US 2009/0069868 A1 Mar. 12, 2009

Related U.S. Application Data

(60) Provisional application No. 60/784,239, filed on Mar. 21, 2006.

(30) Foreign Application Priority Data

Mar. 13, 2006 (EP) .................................. 06111008

(51) Int. Cl.
*A61M 5/142* (2006.01)
*H04B 5/00* (2006.01)
(Continued)

(52) U.S. Cl.
CPC ......... *A61M 5/14248* (2013.01); *H04B 5/0006* (2013.01); *A61M 2205/3569* (2013.01);
(Continued)

(58) Field of Classification Search
CPC ................. A61M 5/14248; A61M 2205/3569; A61M 2205/3592; A61M 2205/6018; H04B 5/0006; A61N 1/08; A61N 1/37211
USPC ..................... 607/2, 60, 31, 32, 30; 455/41.2; 128/903
See application file for complete search history.

(56) References Cited

U.S. PATENT DOCUMENTS 2,605,765 A   8/1952 Kollsman
2,960,097 A   11/1960 Scheffler
(Continued)

FOREIGN PATENT DOCUMENTS

CA   2239457   12/1999
CN   1520626 A   8/2004
(Continued)

OTHER PUBLICATIONS

US 6,197,009, 03/2001, Steg (withdrawn).
(Continued)

*Primary Examiner* — Catherine Voorhees
(74) *Attorney, Agent, or Firm* — Wesley Nicolas

(57) ABSTRACT

The present invention relates to secure paring of electronically controlled devices configured to communicate with each other. A medical system is provided comprising a first unit and a second unit, the system comprising a first communication link allowing a first group of data types to be transmitted between the first unit and the second unit, and a second communication link allowing a second group of data types to be transmitted between the first unit and the second unit. Different properties of the communication links may be used to ensure that certain data, e.g. during pairing of the two devices, can be transmitted in a more controlled way whereas other data can be transmitted in a less controlled way.

26 Claims, 8 Drawing Sheets

(51) Int. Cl.
*A61N 1/08* (2006.01)
*A61N 1/372* (2006.01)

(52) U.S. Cl.
CPC .............. *A61M2205/3592* (2013.01); *A61M 2205/6018* (2013.01); *A61N 1/08* (2013.01); *A61N 1/37211* (2013.01)

(56) References Cited

U.S. PATENT DOCUMENTS

| | | | |
|---|---|---|---|
| 2,980,032 A | 4/1961 | Schneider | |
| 3,705,601 A | 12/1972 | Arisland | |
| 4,016,879 A | 4/1977 | Mellor | |
| 4,077,405 A | 3/1978 | Haerten et al. | |
| 4,137,020 A | 1/1979 | Ito et al. | |
| 4,245,634 A | 1/1981 | Albisser et al. | |
| 4,262,824 A | 4/1981 | Hrynewycz | |
| 4,340,048 A | 7/1982 | Eckenhoff | |
| 4,370,305 A | 1/1983 | Affonso | |
| 4,378,015 A | 3/1983 | Wardlaw | |
| 4,399,824 A | 8/1983 | Davidson | |
| 4,402,407 A | 9/1983 | Maly | |
| 4,519,792 A | 5/1985 | Dawe | |
| 4,529,401 A | 7/1985 | Leslie et al. | |
| 4,544,369 A | 10/1985 | Skakoon et al. | |
| 4,552,561 A | 11/1985 | Eckenhoff et al. | |
| 4,645,491 A | 2/1987 | Evans | |
| 4,657,490 A | 4/1987 | Abbott | |
| 4,710,170 A | 12/1987 | Haber et al. | |
| 4,734,092 A | 3/1988 | Millerd | |
| 4,753,651 A | 6/1988 | Eckenhoff | |
| 4,755,173 A | 7/1988 | Konopka et al. | |
| 4,788,556 A | 11/1988 | Hoisington et al. | |
| 4,871,351 A | 10/1989 | Feingold | |
| 4,877,034 A | 10/1989 | Atkins et al. | |
| 4,886,499 A | 12/1989 | Cirelli et al. | |
| 4,894,054 A | 1/1990 | Miskinyar | |
| 4,928,528 A | 5/1990 | Marques | |
| 4,994,078 A | 2/1991 | Jarvik | |
| 5,008,110 A | 4/1991 | Benecke et al. | |
| 5,049,146 A | 9/1991 | Bringham et al. | |
| 5,076,890 A | 12/1991 | Balembois | |
| 5,122,116 A | 6/1992 | Kriesel et al. | |
| 5,122,201 A | 6/1992 | Frazier et al. | |
| 5,149,340 A | 9/1992 | Waycuilis | |
| 5,169,390 A | 12/1992 | Athayde et al. | |
| 5,211,201 A | 5/1993 | Kamen et al. | |
| 5,224,843 A | 7/1993 | van Lintel | |
| 5,256,157 A | 10/1993 | Samiotes et al. | |
| 5,336,052 A | 8/1994 | Zöllner et al. | |
| 5,390,671 A | 2/1995 | Lord et al. | |
| 5,391,950 A | 2/1995 | Krawczak | |
| 5,482,473 A | 1/1996 | Lord et al. | |
| 5,485,917 A | 1/1996 | Early | |
| 5,494,415 A | 2/1996 | Morita | |
| 5,514,095 A | 5/1996 | Brightbill et al. | |
| 5,527,287 A | 6/1996 | Miskinyar | |
| 5,527,288 A | 6/1996 | Gross et al. | |
| 5,568,806 A | 10/1996 | Cheney, II et al. | |
| 5,584,808 A | 12/1996 | Healy | |
| 5,584,813 A | 12/1996 | Livingston et al. | |
| 5,586,085 A | 12/1996 | Lichte | |
| 5,609,572 A | 3/1997 | Lang | |
| 5,647,853 A | 7/1997 | Feldmann et al. | |
| 5,720,391 A | 2/1998 | Dohm et al. | |
| 5,776,109 A | 7/1998 | Urrutia | |
| 5,814,020 A | 9/1998 | Gross | |
| 5,851,197 A | 12/1998 | Marano et al. | |
| 5,858,001 A | 1/1999 | Tsals et al. | |
| 5,860,952 A | 1/1999 | Quinn | |
| 5,913,856 A | 6/1999 | Chia et al. | |
| 5,925,017 A | 7/1999 | Kriesel et al. | |
| 5,928,194 A | 7/1999 | Maget | |
| 5,931,814 A | 8/1999 | Alex et al. | |
| 5,941,611 A | 8/1999 | Trzmiel et al. | |
| 5,954,643 A | 9/1999 | VanAntwerp et al. | |
| 5,957,895 A | 9/1999 | Sage et al. | |
| 5,968,011 A | 10/1999 | Larsen et al. | |
| 5,997,501 A | 12/1999 | Gross et al. | |
| 6,045,534 A | 4/2000 | Jacobsen et al. | |
| 6,060,319 A | 5/2000 | Deetz et al. | |
| 6,074,369 A | 6/2000 | Sage et al. | |
| 6,083,196 A | 7/2000 | Trautman et al. | |
| 6,088,619 A | 7/2000 | Hein et al. | |
| 6,099,512 A | 8/2000 | Urrutia | |
| 6,120,492 A | 9/2000 | Finch et al. | |
| 6,123,519 A | 9/2000 | Kato et al. | |
| 6,126,637 A | 10/2000 | Kriesel et al. | |
| 6,132,419 A | 10/2000 | Hofmann | |
| 6,132,755 A | 10/2000 | Eicher et al. | |
| 6,165,155 A | 12/2000 | Jacobsen et al. | |
| 6,208,894 B1* | 3/2001 | Schulman et al. | 607/2 |
| 6,241,704 B1 | 6/2001 | Peterson et al. | |
| 6,270,478 B1 | 8/2001 | Mernøe | |
| 6,277,078 B1 | 8/2001 | Porat et al. | |
| 6,280,148 B1 | 8/2001 | Zengerle et al. | |
| 6,293,925 B1 | 9/2001 | Safabash et al. | |
| 6,302,866 B1 | 10/2001 | Marggi | |
| 6,302,869 B1 | 10/2001 | Klitgaard | |
| 6,358,731 B1 | 3/2002 | Hsu | |
| 6,364,865 B1 | 4/2002 | Lavi et al. | |
| 6,485,461 B1 | 11/2002 | Mason et al. | |
| 6,500,150 B1 | 12/2002 | Gross et al. | |
| 6,551,276 B1 | 4/2003 | Mann et al. | |
| 6,554,791 B1 | 4/2003 | Cartledge et al. | |
| 6,555,986 B2 | 4/2003 | Moberg | |
| 6,558,351 B1 | 5/2003 | Steil et al. | |
| 6,585,763 B1 | 7/2003 | Keilman et al. | |
| 6,589,229 B1 | 7/2003 | Connelly et al. | |
| 6,613,015 B2 | 9/2003 | Sandstrom et al. | |
| 6,622,037 B2 | 9/2003 | Kasano | |
| 6,656,159 B2 | 12/2003 | Flaherty | |
| 6,716,192 B1 | 4/2004 | Orosz | |
| 6,720,887 B1* | 4/2004 | Zunti | 340/870.28 |
| 6,740,059 B2 | 5/2004 | Flaherty | |
| 6,749,587 B2 | 6/2004 | Flaherty | |
| 6,808,691 B1 | 10/2004 | Herve et al. | |
| 6,818,178 B2 | 11/2004 | Kohl et al. | |
| 6,878,136 B2 | 4/2005 | Fleury et al. | |
| 6,949,084 B2 | 9/2005 | Marggi et al. | |
| 6,960,192 B1 | 11/2005 | Flaherty et al. | |
| 7,052,483 B2 | 5/2006 | Wojcik | |
| 7,070,580 B2 | 7/2006 | Nielsen | |
| 7,097,631 B2 | 8/2006 | Trautman et al. | |
| 7,097,690 B2 | 8/2006 | Usher et al. | |
| 7,118,531 B2 | 10/2006 | Krill | |
| 7,141,023 B2 | 11/2006 | Diermann et al. | |
| 7,144,384 B2 | 12/2006 | Gorman et al. | |
| 7,303,073 B2 | 12/2007 | Raynal-Olive et al. | |
| 7,643,533 B2 | 1/2010 | McCorkle | |
| 7,738,964 B2* | 6/2010 | Von Arx et al. | 607/60 |
| 7,744,570 B2 | 6/2010 | Fangrow | |
| 7,831,310 B2* | 11/2010 | Lebel et al. | 607/60 |
| 7,881,802 B2* | 2/2011 | Quiles et al. | 607/60 |
| 2001/0025168 A1 | 9/2001 | Gross et al. | |
| 2002/0040083 A1 | 4/2002 | Kuwaki et al. | |
| 2002/0040208 A1 | 4/2002 | Flaherty et al. | |
| 2002/0055711 A1 | 5/2002 | Lavi et al. | |
| 2002/0064468 A1 | 5/2002 | Wade | |
| 2002/0072733 A1 | 6/2002 | Flaherty | |
| 2002/0099412 A1 | 7/2002 | Fischell et al. | |
| 2002/0123740 A1 | 9/2002 | Flaherty et al. | |
| 2002/0161332 A1 | 10/2002 | Ramey | |
| 2002/0169416 A1 | 11/2002 | Gonnelli et al. | |
| 2003/0004411 A1 | 1/2003 | Govari et al. | |
| 2003/0009131 A1 | 1/2003 | Van Antwerp et al. | |
| 2003/0009133 A1 | 1/2003 | Ramey | |
| 2003/0029501 A1 | 2/2003 | Williamson et al. | |
| 2003/0050009 A1 | 3/2003 | Kurisko et al. | |
| 2003/0060781 A1 | 3/2003 | Mogensen et al. | |
| 2003/0065308 A1 | 4/2003 | Lebel et al. | |
| 2003/0069546 A1 | 4/2003 | Sandstrom et al. | |
| 2003/0073952 A1 | 4/2003 | Flaherty et al. | |
| 2003/0088238 A1* | 5/2003 | Poulsen et al. | 604/890.1 |

(56) References Cited

U.S. PATENT DOCUMENTS

| | | |
|---|---|---|
| 2003/0114797 A1 | 6/2003 | Vaillancourt et al. |
| 2003/0114897 A1 | 6/2003 | Von Arx et al. |
| 2003/0114898 A1* | 6/2003 | Von Arx et al. ............... 607/60 |
| 2003/0135159 A1 | 7/2003 | Daily et al. |
| 2003/0167035 A1 | 9/2003 | Flaherty et al. |
| 2003/0187395 A1 | 10/2003 | Gabel et al. |
| 2003/0194328 A1 | 10/2003 | Bryant et al. |
| 2003/0199823 A1 | 10/2003 | Bobroff et al. |
| 2003/0199825 A1 | 10/2003 | Flaherty |
| 2003/0216686 A1 | 11/2003 | Lynch et al. |
| 2003/0236498 A1 | 12/2003 | Gross et al. |
| 2004/0051674 A1 | 3/2004 | Mahringer |
| 2004/0087240 A1 | 5/2004 | Chen et al. |
| 2004/0098068 A1 | 5/2004 | Carbunaru et al. |
| 2004/0115068 A1 | 6/2004 | Hansen et al. |
| 2004/0116905 A1 | 6/2004 | Pedersen et al. |
| 2004/0127844 A1 | 7/2004 | Flaherty |
| 2004/0158207 A1 | 8/2004 | Hunn et al. |
| 2004/0162469 A1 | 8/2004 | Imran |
| 2004/0162521 A1 | 8/2004 | Bengtsson |
| 2004/0171403 A1 | 9/2004 | Mikkola |
| 2004/0199123 A1 | 10/2004 | Nielsen |
| 2004/0203352 A1 | 10/2004 | Hall et al. |
| 2004/0203365 A1 | 10/2004 | Yamamoto et al. |
| 2004/0204673 A1 | 10/2004 | Flaherty et al. |
| 2004/0204744 A1 | 10/2004 | Penner et al. |
| 2004/0210267 A1* | 10/2004 | Lebel et al. ............... 607/32 |
| 2004/0220497 A1 | 11/2004 | Findlay et al. |
| 2004/0220536 A1 | 11/2004 | VanTassel et al. |
| 2004/0260233 A1 | 12/2004 | Garibotto et al. |
| 2005/0006309 A1 | 1/2005 | Effenhauser et al. |
| 2005/0022274 A1 | 1/2005 | Campbell et al. |
| 2005/0077225 A1 | 4/2005 | Usher et al. |
| 2005/0101933 A1 | 5/2005 | Marrs et al. |
| 2005/0136958 A1* | 6/2005 | Seshadri et al. ............... 455/519 |
| 2005/0157896 A1 | 7/2005 | Maltan et al. |
| 2005/0171513 A1 | 8/2005 | Mann et al. |
| 2005/0203461 A1 | 9/2005 | Flaherty et al. |
| 2005/0203582 A1* | 9/2005 | Healy et al. ............... 607/31 |
| 2005/0240154 A1 | 10/2005 | Mogensen et al. |
| 2006/0015063 A1 | 1/2006 | Butikofer et al. |
| 2006/0017576 A1 | 1/2006 | Gordon et al. |
| 2006/0020300 A1 | 1/2006 | Nghiem et al. |
| 2006/0142698 A1 | 6/2006 | Ethelfeld |
| 2006/0143455 A1* | 6/2006 | Gitzinger ............... 713/170 |
| 2006/0200073 A1 | 9/2006 | Radmer et al. |
| 2006/0217694 A1 | 9/2006 | Chin et al. |
| 2006/0264835 A1 | 11/2006 | Nielsen et al. |
| 2006/0267772 A1* | 11/2006 | Knadle et al. ............... 340/572.4 |
| 2007/0021733 A1 | 1/2007 | Hansen et al. |
| 2007/0032195 A1* | 2/2007 | Kurisko et al. ............... 455/41.2 |
| 2007/0073228 A1 | 3/2007 | Mernoe et al. |
| 2007/0104596 A1 | 5/2007 | Preuthun et al. |
| 2007/0112301 A1 | 5/2007 | Preuthun et al. |
| 2008/0009805 A1 | 1/2008 | Ethelfeld |
| 2008/0262573 A1* | 10/2008 | Seeberger et al. ............... 607/60 |
| 2009/0062778 A1* | 3/2009 | Bengtsson et al. ......... 604/890.1 |
| 2009/0163874 A1 | 6/2009 | Krag et al. |

FOREIGN PATENT DOCUMENTS

| | | |
|---|---|---|
| CN | 1612758 | 5/2005 |
| DE | 2552446 | 5/1977 |
| DE | 10255817 | 6/2004 |
| DK | PA 2003 00696 | 5/2003 |
| DK | PA 2003 00697 | 5/2003 |
| EP | 398583 | 11/1990 |
| EP | 568176 | 11/1993 |
| EP | 937475 | 8/1999 |
| EP | 1177802 | 2/2002 |
| EP | 1256356 | 11/2002 |
| EP | 1304661 A1 | 4/2003 |
| EP | 1329233 | 7/2003 |
| EP | 1475113 | 11/2004 |
| EP | 1527792 | 5/2005 |
| EP | 1633104 A1 | 3/2006 |
| EP | 06111008 | 3/2006 |
| EP | 06111011 | 3/2006 |
| EP | 1708405 A1 | 10/2006 |
| EP | 1997233 A1 | 12/2008 |
| GB | 2020735 | 11/1979 |
| GB | 2212387 | 7/1989 |
| JP | 06-209271 A | 7/1994 |
| JP | 2000-104659 | 4/2000 |
| JP | 2000-513259 | 10/2000 |
| JP | 2000-515394 | 11/2000 |
| JP | 2002-505601 | 2/2002 |
| JP | 2003-152606 A | 5/2003 |
| JP | 2003-228618 A | 8/2003 |
| JP | 2005-503242 A | 2/2005 |
| JP | 2005-109720 A | 4/2005 |
| JP | 2005-167946 A | 6/2005 |
| JP | 2005-217646 A | 8/2005 |
| WO | WO 90/07942 | 7/1990 |
| WO | WO 96/07397 | 3/1996 |
| WO | WO 96/30679 | 10/1996 |
| WO | WO 97/21457 | 6/1997 |
| WO | WO 98/57683 | 12/1998 |
| WO | WO 99/62576 | 12/1999 |
| WO | 0010628 A2 | 3/2000 |
| WO | 0019887 A1 | 4/2000 |
| WO | 0074753 A1 | 12/2000 |
| WO | WO 02/02165 | 1/2002 |
| WO | WO 02/04048 | 1/2002 |
| WO | WO 02/05889 | 1/2002 |
| WO | WO 02/15889 | 2/2002 |
| WO | WO 02/15965 | 2/2002 |
| WO | WO 02/40083 | 5/2002 |
| WO | WO 02/45574 | 6/2002 |
| WO | WO 02/47746 | 6/2002 |
| WO | WO 02/055132 | 7/2002 |
| WO | WO 02/070024 | 9/2002 |
| WO | WO 02/081012 | 10/2002 |
| WO | WO 02/100457 | 12/2002 |
| WO | 03005891 A1 | 1/2003 |
| WO | WO 03/026726 | 4/2003 |
| WO | WO 03/026728 | 4/2003 |
| WO | WO 03/080169 | 10/2003 |
| WO | WO 03/089028 | 10/2003 |
| WO | WO 03/090509 | 11/2003 |
| WO | WO 03/099358 | 12/2003 |
| WO | 2004/002572 | 1/2004 |
| WO | WO 2004/009160 | 1/2004 |
| WO | 2004030285 A2 | 4/2004 |
| WO | WO 2004/029457 | 4/2004 |
| WO | WO 2004/030728 | 4/2004 |
| WO | WO 2004/098682 | 11/2004 |
| WO | WO 2004/098683 | 11/2004 |
| WO | WO 2004/098684 | 11/2004 |
| WO | WO 2004/101071 | 11/2004 |
| WO | 2005/000397 A1 | 1/2005 |
| WO | WO 2005/002649 | 1/2005 |
| WO | WO 2005/011779 | 2/2005 |
| WO | WO 2005/025652 | 3/2005 |
| WO | WO 2005/037185 | 4/2005 |
| WO | WO 2005/037350 | 4/2005 |
| WO | WO 2005/039673 | 5/2005 |
| WO | 2005/091546 A2 | 9/2005 |
| WO | WO 2005/094919 | 10/2005 |
| WO | WO 2005/123186 | 12/2005 |
| WO | WO 2005/123189 | 12/2005 |
| WO | 2006/020546 | 2/2006 |
| WO | WO 2006/060277 | 6/2006 |
| WO | WO 2006/067217 | 6/2006 |
| WO | 2006/071364 A1 | 7/2006 |
| WO | WO 2006/077263 | 7/2006 |
| WO | WO 2006/089958 | 8/2006 |
| WO | WO 2006/120253 | 11/2006 |
| WO | WO 2006/123329 | 11/2006 |
| WO | 2007104755 | 9/2007 |

(56) References Cited

FOREIGN PATENT DOCUMENTS

| | | |
|---|---|---|
| WO | 2007104756 A1 | 9/2007 |
| WO | WO 2007/122207 | 11/2007 |
| WO | WO 2009/021950 | 2/2009 |

OTHER PUBLICATIONS

International Search Report mailed Jul. 5, 2007 in international application No. PCT/EP2007/053923.
International Preliminary Examination Report issued in connection with counterpart PCT Application No. PCT/EP2006/062301, mailed Nov. 22, 2007.
International Search Report and Written Opinion issued in connection with counterpart international application No. PCT/EP2006/062301, mailed Nov. 2, 2006.
International Search Report mailed May 24, 2006 in international application No. PCT/EP2006/050410.
Office Action Issued in Connection With Counterpart Danish Application No. PA 2005 00703, Mailed Mar. 3, 2006.
CN 1612758 English Abstract, published Feb. 6, 2008.
DE 10255817 English Abstract, published Jun. 17, 2004.
DE 2552446 English Abstract, published May 26, 1977.
JP 2002-505601 Machine Translation, published Feb. 19, 2002.
JP 2000-515394 Machine Translation, published Nov. 21, 2000.
JP 2000-513259 Machine Translation, published Oct. 10, 2000.
JP 2000-104659 Machine Translation, published Apr. 11, 2000.
Final Office Action mailed Apr. 16, 2010 in U.S. Appl. No. 12/303,307, filed Feb. 20, 2009 by Krag.
Non-Final Office Action mailed Nov. 27, 2009 in U.S. Appl. No. 12/303,307, filed Feb. 20, 2009 by Krag.
Non-Final Office Action mailed Apr. 6, 2010 in U.S. Appl. No. 12/298,253, filed Dec. 8, 2008 by Krag et al.
Final Office Action mailed Apr. 28, 2010 in U.S. Appl. No. 12/066,712, filed Mar. 13, 2008 by Hansen et al.
Non-Final Office Action mailed Oct. 27, 2009 in U.S. Appl. No. 12/066,712, filed Mar. 13, 2008 by Hansen et al.
Non-Final Office Action mailed Apr. 10, 2009 in U.S. Appl. No. 12/066,712, filed Mar. 13, 2008 by Hansen et al.
Final Office Action mailed Jul. 16, 2010 in U.S. Appl. No. 11/913,689, filed Dec. 12, 2007 by Hansen et al.
Non-Final Office Action mailed Mar. 15, 2010 in U.S. Appl. No. 11/913,689, filed Dec. 12, 2007 by Hansen et al.
Final Office Action mailed Nov. 25, 2009 in U.S. Appl. No. 11/913,689, filed Dec. 12, 2007 by Hansen et al.
Non-Final Office Action mailed May 8, 2009 in U.S. Appl. No. 11/913,689, filed Dec. 12, 2007 by Hansen et al.
Non-Final Office Action mailed Apr. 30, 2010 in U.S. Appl. No. 11/911,213, filed Oct. 11, 2007 by Nielsen et al.
Non-Final Office Action mailed Jul. 24, 2009 in U.S. Appl. No. 11/911,213, filed Oct. 11, 2007 by Nielsen et al.
Final Office Action mailed Nov. 17, 2009 in U.S. Appl. No. 11/816,729, filed Nov. 15, 2007 by Larsen et al.
Non-Final Office Action mailed Apr. 17, 2009 in U.S. Appl. No. 11/816,729, filed Nov. 15, 2007 by Larsen et al.
Non-Final Office Action mailed Jul. 23, 2010 in U.S. Appl. No. 11/813,433, filed Apr. 30, 2008 by Teisen-Simony et al.
Non-Final Office Action mailed Apr. 28, 2010 in U.S. Appl. No. 11/813,381, filed Apr. 11, 2008 by Teisen-Simony et al.
Final Office Action mailed Nov. 3, 2009 in U.S. Appl. No. 11/792,355, filed Apr. 23, 2008 by Ethelfeld et al.
Non-Final Office Action mailed Feb. 17, 2009 in U.S. Appl. No. 11/792,355, filed Apr. 23, 2008 by Ethelfeld et al.
Final Office Action mailed Dec. 29, 2009 in U.S. Appl. No. 11/663,048, filed Nov. 15, 2007 by Thorkild et al.
Non-Final Office Action mailed Apr. 17, 2009 in U.S. Appl. No. 11/663,048, filed Nov. 15, 2007 by Thorkild et al.
Notice of Abandonment mailed Oct. 23, 2007 in U.S. Appl. No. 11/662,905, filed Sep. 22, 2005 by Ahm et al.
Non-Final Office Action mailed May 19, 2010 in U.S. Appl. No. 11/541,348, filed Sep. 29, 2006 by Preuthun et al.
Final Office Action mailed Jan. 8, 2010 in U.S. Appl. No. 11/541,348, filed Sep. 29, 2006 by Preuthun et al.
Non-Final Office Action mailed May 22, 2009 in U.S. Appl. No. 11/541,348, filed Sep. 29, 2006 by Preuthun et al.
Response and Amendment filed Jan. 29, 2009 in U.S. Appl. No. 11/541,348, filed Sep. 29, 2006 by Preuthun et al.
Final Office Action mailed Oct. 29, 2008 in U.S. Appl. No. 11/541,348, filed Sep. 29, 2006 by Preuthun et al.
Response and Amendment filed Jul. 16, 2008 in U.S. Appl. No. 11/541,348, filed Sep. 29, 2006 by Preuthun et al.
Non-Final Office Action mailed Apr. 18, 2008 in U.S. Appl. No. 11/541,348, filed Sep. 29, 2006 by Preuthun et al.
Final Office Action mailed May 5, 2010 in U.S. Appl. No. 11/540,842, filed Sep. 29, 2006 by Preuthun et al.
Non-Final Office Action mailed Sep. 28, 2009 in U.S. Appl. No. 11/540,842, filed Sep. 29, 2006 by Preuthun et al.
Response and Amendment filed Aug. 7, 2009 in U.S. Appl. No. 11/540,842, filed Sep. 29, 2006 by Preuthun et al.
Final Office Action mailed May 13, 2009 in U.S. Appl. No. 11/540,842, filed Sep. 29, 2006 by Preuthun et al.
Response and Amendment filed Mar. 11, 2009 in U.S. Appl. No. 11/540,842, filed Sep. 29, 2006 by Preuthun et al.
Non-Final Office Action mailed Dec. 12, 2008 in U.S. Appl. No. 11/540,842, filed Sep. 29, 2006 by Preuthun et al.
Response and Amendment filed Oct. 10, 2008 in U.S. Appl. No. 11/540,842, filed Sep. 29, 2006 by Preuthun et al.
Final Office Action mailed Jul. 11, 2008 in U.S. Appl. No. 11/540,842, filed Sep. 29, 2006 by Preuthun et al.
Response and Amendment filed May 20, 2008 in U.S. Appl. No. 11/540,842, filed Sep. 29, 2006 by Preuthun et al.
Non-Final Office Action mailed Feb. 25, 2008 in U.S. Appl. No. 11/540,842, filed Sep. 29, 2006 by Preuthun et al.
Final Office Action mailed Aug. 5, 2009 in U.S. Appl. No. 11/407,647, filed Apr. 20, 2006 by Hansen et al.
Non-Final Office Action mailed Feb. 6, 2009 in U.S. Appl. No. 11/407,647, filed Apr. 20, 2006 by Hansen et al.
Final Office Action mailed Sep. 29, 2008 in U.S. Appl. No. 11/407,647, filed Apr. 20, 2006 by Hansen et al.
Non-Final Office Action mailed Feb. 28, 2008 in U.S. Appl. No. 11/407,647, filed Apr. 20, 2006 by Hansen et al.
Non-Final Office Action mailed Aug. 19, 2010 in U.S. Appl. No. 11/266,905, filed Nov. 4, 2005 by Ethelfeld et al.
Final Office Action mailed Oct. 30, 2009 in U.S. Appl. No. 11/266,905, filed Nov. 4, 2005 by Ethelfeld et al.
Non-Final Office Action mailed Mar. 18, 2009 in U.S. Appl. No. 11/266,905, filed Nov. 4, 2005 by Ethelfeld et al.
Non-Final Office Action mailed Aug. 25, 2008 in U.S. Appl. No. 11/266,905, filed Nov. 4, 2005 by Ethelfeld et al.
Final Office Action mailed Oct. 5, 2007 in U.S. Appl. No. 11/266,905, filed Nov. 4, 2005 by Ethelfeld et al.
Non-Final Office Action mailed Mar. 27, 2007 in U.S. Appl. No. 11/266,905, filed Nov. 4, 2005 by Ethelfeld et al.
Notice of Abandonment mailed Oct. 12, 2010 in U.S. Appl. No. 11/266,904, filed Nov. 4, 2005 by Ethelfeld et al.
Second Advisory Action mailed Aug. 13, 2008 in U.S. Appl. No. 11/266,904, filed Nov. 4, 2005 by Ethelfeld et al.
First Advisory Action mailed Dec. 28, 2007 in U.S. Appl. No. 11/266,904, filed Nov. 4, 2005 by Ethelfeld et al.
Final Office Action mailed Sep. 11, 2007 in U.S. Appl. No. 11/266,904, filed Nov. 4, 2005 by Ethelfeld et al.
Non-Final Office Action mailed Jan. 5, 2007 in U.S. Appl. No. 11/266,904, filed Nov. 4, 2005 by Ethelfeld et al.
Requirement for Restriction mailed May 22, 2006 in U.S. Appl. No. 11/266,904, filed Nov. 4, 2005 by Ethelfeld et al.
Notice of Allowance mailed Jul. 15, 2009 in U.S. Appl. No. 11/266,821, filed Nov. 4, 2005 by Ethelfeld et al.
Non-Final Office Action mailed Jan. 29, 2009 in U.S. Appl. No. 11/266,821, filed Nov. 4, 2005 by Ethelfeld et al.
Final Office Action mailed Jul. 18, 2008 in U.S. Appl. No. 11/266,821, filed Nov. 4, 2005 by Ethelfeld et al.
Non-Final Office Action mailed Mar. 28, 2008 in U.S. Appl. No. 11/266,821, filed Nov. 4, 2005 by Ethelfeld et al.

(56) References Cited

OTHER PUBLICATIONS

Final Office Action mailed Oct. 16, 2009 in U.S. Appl. No. 11/250,233, filed Oct. 14, 2005 by Ethelfeld et al.
Non-Final Office Action mailed Mar. 12, 2009 in U.S. Appl. No. 11/250,233, filed Oct. 14, 2005 by Ethelfeld et al.
Notice of Abandonment mailed Aug. 31, 2010 in U.S. Appl. No. 10/566,795, filed Aug. 30, 2006 by Radmer et al.
Final Office Action mailed May 4, 2009 in U.S. Appl. No. 10/566,795, filed Aug. 30, 2006 by Radmer et al.
Non-Final Office Action mailed Oct. 17, 2008 in U.S. Appl. No. 10/566,795, filed Aug. 30, 2006 by Radmer et al.
Philips T G, How NFC can to speed Bluetooth transactions-today, EE times, Year 2006.
Sufi F. et al. A Mobile Phone Based Intelligent Telemonitoring Platform,Proceedings of the 3rd IEEE-EMBS International Summer School and Symposium on Medical Devices and Biosensors, Year 2006, pp. 101-104.
Specification of the Bluetooth system. V 1.0 Year 1999.
Haartsen J, Bluetooth- The universal radio interlace for ad hoc, wireless connectivity, Ericsson Review No. 3, Year 1998 pp. 110-117.
Bluetooth: The Future of Wireless Medical Technology?, MDDI Medical Device and Diagnostic Industry News Products and Suppliers. Year 2002.
SalminenT et al.Enhancing Bluetooth Connectivity with RFID, Proceedings of the Fourth Annual IEEE International Conference on Pervasive Computing and Communications Year 2006.
Tura A. et al. Medical Wearable Device with Wireless Bluetooth-based data Transmission, Measurement Science Review, Year 2003 vol. 3, Section 2, pp. 1-4.
Medical Applications of Wireless Technology, University of Missouri-Rolla, Year 2005.
Press release connectBlue, FDA approves first medical system using Bluetooth wireless technology Year Sep. 9, 2003.
Extract from EP register for EP1997234, Jul. 2013.

* cited by examiner

Fig. 6
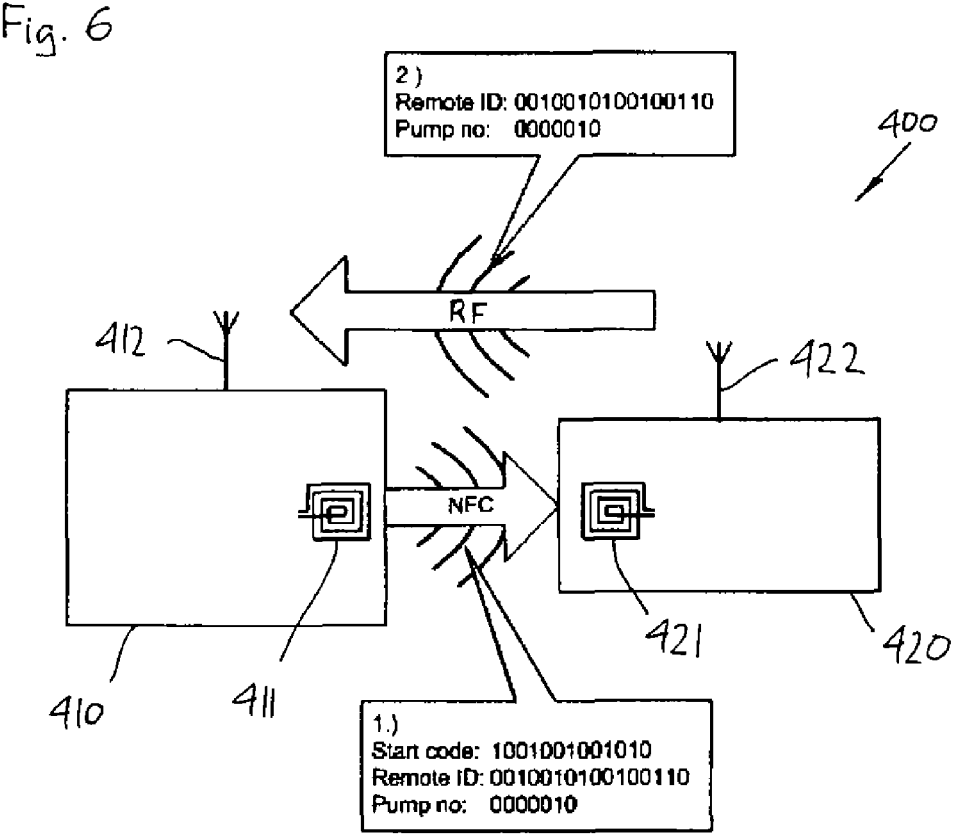
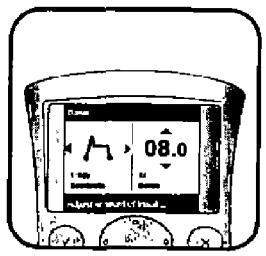
Fig. 9A
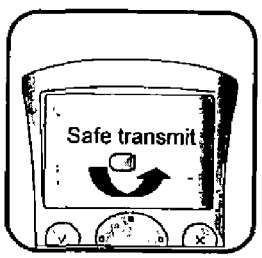
Fig. 9B
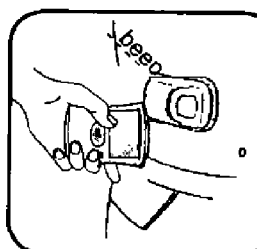
Fig. 9C
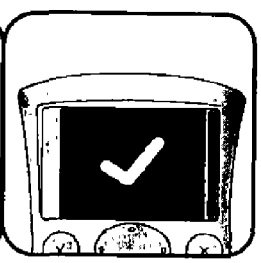
Fig. 9D

SECURE PAIRING OF ELECTRONIC DEVICES USING DUAL MEANS OF COMMUNICATION

CROSS-REFERENCE TO RELATED APPLICATIONS

This application is a 35 U.S.C. §371 national stage application of International Patent Application PCT/EP2007/052336 (published as WO 2007/104755), filed Mar. 13, 2007, which claimed priority of European Patent Application 06111008.6, filed Mar. 13, 2006; this application further claims priority under 35 U.S.C. §119 of U.S. Provisional Application 60/784,239, filed Mar. 21, 2006.

The present invention generally relates to the secure pairing of two electronically controlled devices adapted to communicate with each other. In a specific embodiment the invention relates to a medical delivery device in combination with a control unit for controlling the delivery device, however, the invention is applicable for all types of devices for which a secure pairing is an issue.

BACKGROUND OF THE INVENTION

In the disclosure of the present invention reference is mostly made to the treatment of diabetes by infusion of insulin, however, this is only an exemplary use of the present invention.

Portable drug delivery devices for delivering a drug to a patient are well known and generally comprise a reservoir adapted to contain a liquid drug, a pump assembly for expelling a drug out of the reservoir and through the skin of the subject via a transcutaneous access device such as a soft cannula or a needle. Such devices are often termed infusion pumps.

Basically, infusion pumps can be divided into two classes. The first class comprises durable infusion pumps which are relatively expensive pumps intended for 3-4 years use, for which reason the initial cost for such a pump often is a barrier to this type of therapy. Although more complex than traditional syringes and pens, the pump offer the advantages of continuous infusion of insulin, precision in dosing and optionally programmable delivery profiles and user actuated bolus infusions in connections with meals. Such pumps are normally carried in a belt or pocket close to the body.

Addressing the above cost issue, several attempts have been made to provide a second class of drug infusion devices that are low in cost yet convenient to use. Some of these devices are intended to be partially or entirely disposable and may provide many of the advantages associated with an infusion pump without the attendant costs. For example, U.S. Pat. No. 6,589,229 discloses a skin-mountable drug infusion device which may have a two-part construction in which more expensive electronic components are housed in a reusable portion and the fluid delivery components are housed in a separable disposable portion (i.e. intended for single use only). U.S. Pat. No. 6,656,159 discloses a skin-mountable drug infusion device which is fully disposable.

The traditional durable pump may be worn in a belt at the waist of the user, this allowing the user to operate the pump by directly accessing the user interface on the pump, e.g. in order to change infusion rate or to program a bolus infusion. However, the pump may also be worn hidden under clothing making this operation more difficult.

Correspondingly, it has been proposed to provide an infusion pump of the durable type with a wireless remote controller allowing the user to access some or all of the functionality of the pump, see for example U.S. Pat. No. 6,551,276, US 2003/0065308, US 2005/0022274, US 2005/0171513, US 2006/0017576 and US 2006/0020300, which are hereby incorporated by reference. The pump and controller may be adapted to communicate with further devices, e.g. US 2005/0171513 discloses a remote controller which may also communicate with external devices such as a glucose monitor, cell phone, PDA or computer using its RF transmitter/receiver, US 2006/0017576 discloses an implantable pump which has two different communication means allowing it to communicate with two different external control devices, and US 2006/0020300 discloses an implantable device to which an external antenna can be coupled to increase communication distance before implantation.

For a skin-mountable device, typically comprising an adhesive allowing the device to be attached directly to the skin of the user, a remote controller would appear even more desirable. Correspondingly, U.S. Pat. No. 6,589,229 and U.S. Pat. No. 6,740,059, which are hereby incorporated by reference, disclose semi-disposable and fully disposable infusion devices (which may be termed a local device or unit) which are intended to be operated primarily or entirely by a wireless remote controller (which may be termed a remote device or unit). As the delivery device thus does not have to be provided with a user interface such as a display and keyboard, the semi-disposable or disposable infusion can be provided more cost-effectively.

In order to provide safe operation of a given delivery device it is of utmost importance that control commands sent from a given remote control unit only control actuation of the specific delivery device it is intended to control, and not some other delivery device in the proximity of the user. Further, as the delivery device may be adapted to transmit information back to the remote controller, it is also essential that such information is only received by the corresponding control unit. This issue is applicable to both durable systems and systems comprising disposable units. To provide the desired security the two devices intended to work together will normally be "paired" by exchange of information between the two devices, this allowing the information sent between the two devices to be specifically coded and thus only accepted by the correspondingly coded device. As appears, when a specific remote controller is to be paired with a specific delivery device it is of utmost importance that it is in fact the two devices which are intended to be paired that are actually paired—and not that the remote controller is accidentally being paired with a neighboring delivery. During a pairing process other information may also be transmitted between the two devices, e.g. the controller may be provided with information as to the type of delivery device in case different types of delivery devices are intended to be used with a given remote controller.

However, even if a remote controller has been correctly paired with a given delivery device, it may still be possible to control the delivery device in an undesired way. For example, if a remote controller comes into the hands of a third person, it may be possible for that person to control the delivery device, typically without the knowledge of the user of the delivery device. For example, a child may find the remote controller and start to play with it, this resulting in the inadvertently transmission of infusion commands to the delivery device, e.g. the infusion of a bolus of insulin.

Having regard to the above, it is the object of the present invention to provide devices and methods allowing secure pairing of two electronically controlled devices adapted to communicate with each other, either one-way or two-way. It is a further object of the invention to provide such devices and methods which provide safety of use and which to a high degree protect against the inadvertent transmission of data, e.g. commands, between two electronically controlled devices.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect a medical system is provided comprising a first unit and a second unit, the system comprising first means of communication allowing a first group of data types to be transmitted between the first unit and the second unit, and second means of communication allowing a second group of data types to be transmitted between the first unit and the second unit. In this way different properties of the two means of communication can be used to secure that certain data, e.g. during pairing of the two devices, can be transmitted in a more controlled way whereas other data can be transmitted in a less controlled way. The system may comprise additional units just as it may comprise additional means of communication. Although the data of the two defined groups are transmitted using the two different means of communication, a third group of data may be provided which can be transmitted using either of the two means of communication. Such a third group of data may also be considered to represent "overlapping" members of first and second groups of data. Indeed, the first and second groups cannot be fully overlapping as this would render the definition of two groups meaningless. The determination of which data type is arranged in which group may be preset, or the group for some or all of the data types may be selectable, e.g. by a physician.

The two groups of data types may comprise partly overlapping members, e.g. at least one data type may only be transmitted by one of the first and second means of communication, and at least one data type may be transmitted by both of the first and second means of communication.

In an exemplary embodiment at least one means of communication comprises a wireless transmitter and corresponding receiver. For example, the first means of communication may be selected from the group comprising RF communication, optical communication, ultrasonic communication, induction and a galvanic contact, and the second means of communication may be selected from the group comprising RF communication, ultrasonic communication, and optical communication.

To control transmission of data, the first means of communication may have a shorter range of communication than the second means of communication under given conditions. For example, under the given conditions the first means of communication may be NFC (near-field communication) having a range of communication less than 0.5 meter, preferably less than 0.2 meter and most preferably less than 0.1 meter, and the second means of communication has a range of communication of more than 0.5 meter, preferably more than 1 meter and most preferably more than 3 meter. The "given conditions" would normally be such conditions that can be found in a normal home or work environment, e.g. as in an office. Both the first and second means of communication may be by wireless communication. For example, the first means of communication may be RF communication at a frequency of less than 24 MHz, and the second means of communication may be RF communication at a frequency of more than 24 MHz.

By using NFC between the first and second units for some type of data, a high degree of protection against inadvertent pairing of units can be provided. Correspondingly, the first group of data types may comprise a unique ID for the second unit, which ID can then only be received by the intended first unit when the two units are in close proximity of each other. To further enhance safety also the second group of data types may comprise a unique ID for the first unit which is then transmitted to the second unit in return for the first ID. Further, to protect against the unintended use of e.g. a remote controller to control a drug delivery device, the first group of data types may comprise an activation (or authorisation) command, the first unit being adapted to allow one or more types of commands from the second group of data types to be received and executed for a given period of time after an activation command has been received. For example, to send a bolus command to a drug delivery device the remote controller would first have to brought close to a given drug delivery device and an activation command transmitted, this action opening a time window of e.g. 5 minutes in which a bolus command will be accepted by the drug delivery device when received using the second means of communication.

At least one of the means of communication may provide uni-directional communication only between the two units. For example, in an advanced drug delivery system using the second means of communication commands bi-directionally, instructions and programs may be transmitted from a remote controller to a drug delivery device, just as e.g. acknowledgement, status and error information may be transmitted from the drug delivery device to the remote controller. However, transmission of pairing information and activation commands may require the first means of communication to be only uni-directionally.

In an exemplary embodiment the medical system may comprise an acoustic transducer (e.g. loudspeaker) having a transducer coil with a plurality of windings, the transducer coil serving as a receiver for wireless inductive signals, e.g. RF signals. In this way a "parasite" property of the acoustic transducer can be used, i.e. using the coil as a receiving means, thereby replacing a receiving structure, e.g. a separate receiver coil or an antenna, which would otherwise have to be provided, this reducing manufacturing costs.

The different aspects of the present invention may be adapted in a wide range of systems in which safe pairing of units is of importance and the two units may correspondingly have any desirable functionality. For example, the first unit may be a process unit adapted to process received data, e.g. a drug delivery device adapted to deliver an amount of drug in accordance with received instructions, or a sensor device adapted to process and/or transmit sensor data from an associated sensor, and the second unit may be a remote controller adapted to e.g. transmit instructions or to receive and store sensor data. Each of the units may be of unitary construction or it may be adapted to be used in combination with one or more further units or means.

Thus, a medical system is provided in which a process unit comprises a process unit transmitter, a process unit receiver, and a process unit processor connected to the process unit transmitter, the process unit receiver and the transducer coil. A controller unit comprises a first controller unit transmitter adapted to transmit information to the transducer coil, a second controller unit transmitter adapted to transmit information to the process unit receiver, a controller unit receiver adapted for receiving information from the process unit transmitter, and a controller unit processor connected to the first and second controller unit transmitters and the controller unit receiver, wherein the first means of communication comprises the transducer coil and the first controller unit transmitter, and the second means of communication comprises the process unit transmitter, the process unit receiver, the second controller unit transmitter, and the controller unit receiver.

In the context of the present application and as used in the specification and claims, the term processor covers any combination of electronic circuitry suitable for providing the specified functionality, e.g. processing data and controlling memory as well as all connected input and output devices. The processor will typically comprise one or more CPUs or microprocessors which may be supplemented by additional devices for support or control functions. For example, a transmitter or a receiver may be fully or partly integrated with the processor, or may be provided by individual units. Each of the components making up the processor circuitry may be special purpose or general purpose devices.

The process unit may comprise a reservoir adapted to contain a fluid drug, an expelling assembly adapted for cooperation with the reservoir to expel fluid drug from the reservoir to a subject via an outlet, and processor means for controlling the expelling assembly. The reservoir may be any suitable structure adapted to hold an amount of a fluid drug, e.g. a hard reservoir, a flexible reservoir, a distensible or elastic reservoir. The reservoir may e.g. be pre-filled, user-fillable or in the form of a replaceable cartridge which again may be prefilled or fillable. The expelling assembly may be of any desired type, e.g. a membrane pump, a piston-cylinder pump or a roller-tube pump. Advantageously, the processor means is adapted to receive flow instructions from a control unit, the control unit comprising a user interface allowing a user to enter flow instruction for subsequent transmission to the process unit, e.g. programming a basal infusion rate profile or a bolus. The process unit may be adapted to be implanted or the outlet may comprise or be adapted to connect to a transcutaneous access device, thereby allowing a fluid drug to be expelled out of the reservoir and through the skin of the subject via the transcutaneous access device. In such a medical system the first group of data types may comprise at least one type of command controlling the delivery of an amount of fluid drug to the subject. For example, when a user desires to program a bolus infusion of a drug such as insulin, such an instruction can only be transmitted to the process unit when the remote controller is moved into the vicinity thereof, this preventing to a high degree that other people will be able to pick up a given remote controller and inadvertently transmit a bolus or other infusion command to a drug delivery device controlled by that remote controller.

Alternatively, the first unit may comprise a processor adapted to transmit and/or process data acquired via a sensor device, and may include a transcutaneous sensor device adapted for cooperation with the processor.

The medical system of the invention may further comprise a transcutaneous device unit comprising a transcutaneous device, e.g. access device or sensor device, a mounting surface adapted for application to the skin of a subject, e.g. an adhesive surface, wherein the transcutaneous device unit and the first unit are adapted to be secured to each other to form a combined device.

In the above embodiments of the invention a system comprising first and second units has been described, however, the present invention also provides such units per se.

Thus, a medical unit is provided comprising first means of communication allowing a first group of data types to be transmitted between the unit and a further unit, and second means of communication allowing a second group of data types to be transmitted between the unit and the further unit.

In exemplary embodiments the medical unit may be in the form of any of the above-described first and second units, such first and second unit being adapted to communicate with a corresponding second or first unit as described.

In a further aspect of the invention, a medical system is provided comprising a first unit and a second unit, the system comprising first means of communication allowing a first group of data types to be transmitted between the first unit and the second unit. The first unit further comprises an element serving a first purpose, wherein a parasite property of the element serves as a wireless receiver. The element may be a metal chassis part serving also as an antenna, or, as described below, a loudspeaker in which the coil is used to pick up induction signals.

Thus, in a specific aspect of the invention, a medical system is provided comprising a first unit and a second unit, the system comprising first means of communication allowing a first group of data types to be transmitted between the first unit and the second unit, the first unit comprising an acoustic transducer having a transducer coil with a plurality of windings, the transducer coil serving as a receiver for wireless inductive signals. In this way a "parasite" property of the acoustic transducer can be used, i.e. using the coil as a receiving means, thereby replacing a receiving structure, e.g. a separate receiver coil or an antenna, which would otherwise have to be provided, this reducing manufacturing costs. The term "first" merely denotes that further means of communication may be provided.

The first unit may be a process unit comprising a process unit processor connected to the transducer coil, and the second unit may be a controller unit comprising a first controller unit transmitter adapted to transmit information to the transducer coil, and a controller unit processor connected to the first controller unit transmitter, wherein the first means of communication comprises the transducer coil and the first controller unit transmitter.

The medical system may further comprise second means of communication allowing a second group of data types to be transmitted between the first unit and the second unit. The first means of communication may have a shorter range of communication than the second means of communication under given conditions. The second means of communication may be either RF or optical communication. Under the given conditions the first means of communication may have a range of communication less than 0.5 meter, and the second means of communication has a range of communication of more than 0.5 meter. The first means of communication may use RF communication at a frequency of less than 24 MHz, and the second means of communication may use RF communication at a frequency of more than 24 MHz.

In an exemplary embodiment a medical system is provided as disclosed above, in which both the first and second means of communication provides uni-directional communication only between the two units. In such a system the first unit may be a process unit comprising a process unit receiver, and a process unit processor connected to the process unit receiver and the transducer coil. The second unit may be a controller unit comprising a first controller unit transmitter adapted to transmit information to the transducer coil, a second controller unit transmitter adapted to transmit information to the process unit receiver, and a controller unit processor connected to the first and second controller unit transmitters, wherein the first means of communication comprises the transducer coil and the first controller unit transmitter, and the second means of communication comprises the process unit receiver and the second controller unit transmitter.

In another exemplary embodiment a medical system is provided as disclosed above, in which the first means of communication provides uni-directional communication from the second unit to the first unit, and the second means of communication provides bi-directional communication between the first unit and the second unit. In such a system the first unit may be a process unit comprising a process unit transmitter, a process unit receiver, and a process unit processor connected to the process unit transmitter, the process unit receiver and the transducer coil. The second unit may be a controller unit comprising a first controller unit transmitter adapted to transmit information to the transducer coil, a second controller unit transmitter adapted to transmit information to the process unit receiver, a controller unit receiver adapted for receiving information from the process unit transmitter, and a controller unit processor connected to the first and second controller unit transmitters and the controller unit receiver, wherein the first means of communication comprises the transducer coil and the first controller unit transmitter, and the second means of communication comprises the process unit transmitter, the process unit receiver, the second controller unit transmitter, and the controller unit receiver.

In the above-described medical systems the first group of data types may comprise a unique ID for the second unit and/or a time stamp. The first group of data types may also comprise an activation command, the first unit being adapted to allow one or more types of commands from the second group of data types to be received and executed for a given period of time after an activation command has been received.

In an exemplary embodiment a medical system as described above is provided in which the first unit comprises a reservoir adapted to contain a fluid drug, an expelling assembly adapted for cooperation with the reservoir to expel fluid drug from the reservoir to a subject via an outlet, and processor means for controlling the expelling assembly.

In the above embodiments of the invention in accordance with the further aspect of the invention a system comprising first and second units has been described, however, the present invention also provides such units per se.

Thus, a medical unit is provided comprising first means of communication allowing a first group of data types to be transmitted between the unit and a further unit, the first unit comprising an acoustic transducer having a transducer coil with a plurality of windings, the transducer coil serving as a receiver for wireless inductive signals. In exemplary embodiments the medical unit may be in the form of any of the above-described first and second units, such first and second unit being adapted to communicate with a corresponding second or first unit as described.

The invention further provides a method of operating a medical system comprising first and second units, the method comprising the steps of (i) providing a medical system having first and second units, (ii) transmitting a first group of data types between the first unit and the second unit using first means of communication, and (iii) transmitting a second group of data types between the first unit and the second unit using second means of communication. One or both means of communication may be wireless.

As used herein, the term "drug" is meant to encompass any drug-containing flowable medicine capable of being passed through a delivery means such as a cannula or hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject.

BRIEF DESCRIPTION OF THE DRAWINGS

In the following the invention will be further described with reference to the drawings, wherein FIG. 6 shows a further schematic representation of a local unit and a remote unit, FIGS. 9A-9D show steps of transmitting a command between two medical units.

In the figures like structures are mainly identified by like reference numerals.

DESCRIPTION OF EXEMPLARY EMBODIMENTS

When the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as their relative dimensions are intended to serve illustrative purposes only.

Before turning to the present invention per se, a system suitable to be used in combination therewith will be described, the system comprising a pump unit (i.e. local unit), a patch unit adapted to be used in combination with the pump unit, and a remote control unit for wireless communication with the pump unit. However, the present invention may be used in any system or unit in which the features of the present invention would be relevant, e.g. in a conventional durable infusion pump or system, or in a sensor system.

Figure 2:
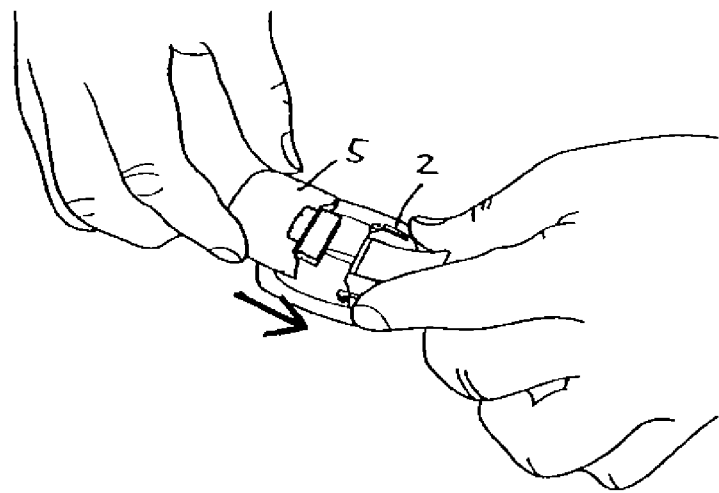
Figure 3:
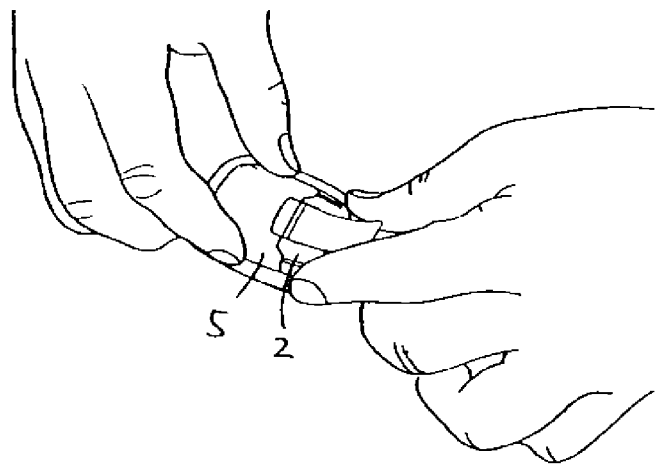

Firstly, with reference to FIGS. 1-3 an embodiment of a medical device for drug delivery will be described focusing primarily on the directly user-oriented features during application of the device to a skin surface. The patch unit 2 comprises a transcutaneous device in the form of a hollow infusion device, e.g. a needle or soft cannula, however, the needle or cannula may be replaced with any desirable transcutaneous device suitable for delivery of a fluid drug or for sensing a body parameter.

Figure 1:
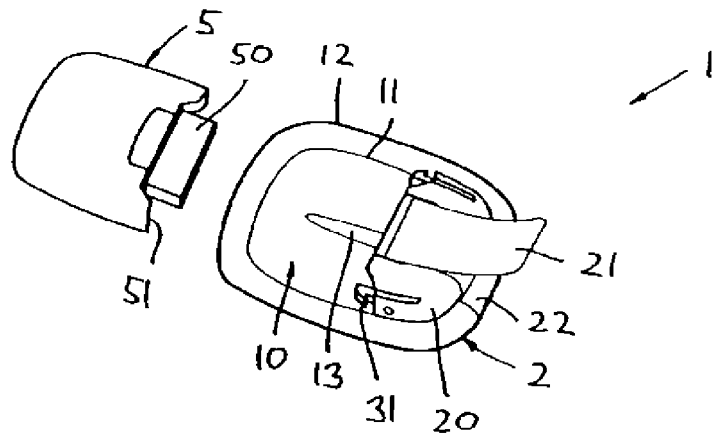
FIGS. 1-3 shows in perspective views sequences of use for a first embodiment of a drug delivery device.

More specifically, FIG. 1 shows a perspective view of medical device in the form of a modular skin-mountable drug delivery device 1 comprising a patch unit 2 and a pump unit 5 (as the pump unit comprises a reservoir it may also be termed a reservoir unit). When supplied to the user each of the units are preferably enclosed in its own sealed package (not shown). The embodiment shown in FIG. 1 comprises a patch unit provided with an insertable transcutaneous device, e.g. needle, cannula or sensor. In case an actual embodiment requires the patch unit to be mounted on the skin and the transcutaneous device inserted before a pump or other unit can be attached, it follows that the method of use would be adopted correspondingly.

The patch unit comprises a flexible patch portion 10 with a lower adhesive mounting surface 12 adapted for application to the skin of a user, and a housing portion 20 in which a transcutaneous device (not shown) is arranged. The transcutaneous device comprises a pointed distal end adapted to penetrate the skin of a user, and is adapted to be arranged in fluid communication with the pump unit. In the shown embodiment the pointed end of the transcutaneous device is moveable between an initial position in which the pointed end is retracted relative to the mounting surface, and an extended position in which the pointed end projects relative to the mounting surface. The transcutaneous device may also be moveable between the extended position in which the distal end projects relative to the mounting surface, and a retracted position in which the distal end is retracted relative to the mounting surface.

The patch unit further comprises user-gripable actuation means in the form of a first strip-member 21 for moving the transcutaneous device between the initial and the second position when the actuation means is actuated, and a user-gripable second strip-member 22 for removing the patch from the skin surface. The second strip may also be used to move the distal end of the transcutaneous device between the extended and the retracted position. The housing further comprises user-actuatable male coupling means 31 in the form of a pair of resiliently arranged hook members adapted to cooperate with corresponding female coupling means 51 on the pump unit, this allowing the pump unit to be releasable secured to the patch unit in the situation of use. A flexible ridge formed support member 13 extends from the housing and is attached to the upper surface 11 of the patch. The adhesive surface is supplied to the user with a peelable protective sheet.

The pump unit 5 comprises a pre-filled reservoir containing a liquid drug formulation (e.g. insulin) and an expelling assembly for expelling the drug from the reservoir through the needle in a situation of use. The reservoir unit has a generally flat lower surface adapted to be mounted onto the upper surface of the patch portion, and comprises a protruding portion 50 adapted to be received in a corresponding cavity of the housing portion 20 as well as female coupling means 51 adapted to engage the corresponding hook members 31 on the needle unit. The protruding portion provides the interface between the two units and comprises a pump outlet and contact means (not shown) allowing the pump to detect that it has been assembled with the patch.

In a situation of use the user assembles the two units which are then mounted on a skin surface where after the transcutaneous device is inserted and the pump is ready to operate. Operation may start automatically as the transcutaneous device is inserted, or the pump may be started via the remote unit, see below. Before the pump unit is mounted to the patch unit, the user will normally have paired the pump unit with the remote unit, see below. In an alternative situation of use the user may first mount the patch unit to a skin surface and insert the transcutaneous device, after which the pump unit is mounted to the patch unit.

After the assembled device has been left in place for the recommended period of time for use of the patch unit (e.g. 48 hours)—or in case the reservoir runs empty or for other reasons—it is removed from the skin by gripping and pulling the retraction strip 22 which may also lead to retraction of the transcutaneous device. The pump unit may be removed from the patch unit before or after the patch unit is removed from the skin. Thereafter the pump unit can be used again with fresh patch units until it has been emptied or the patch has to be changed again.

Figure 4:
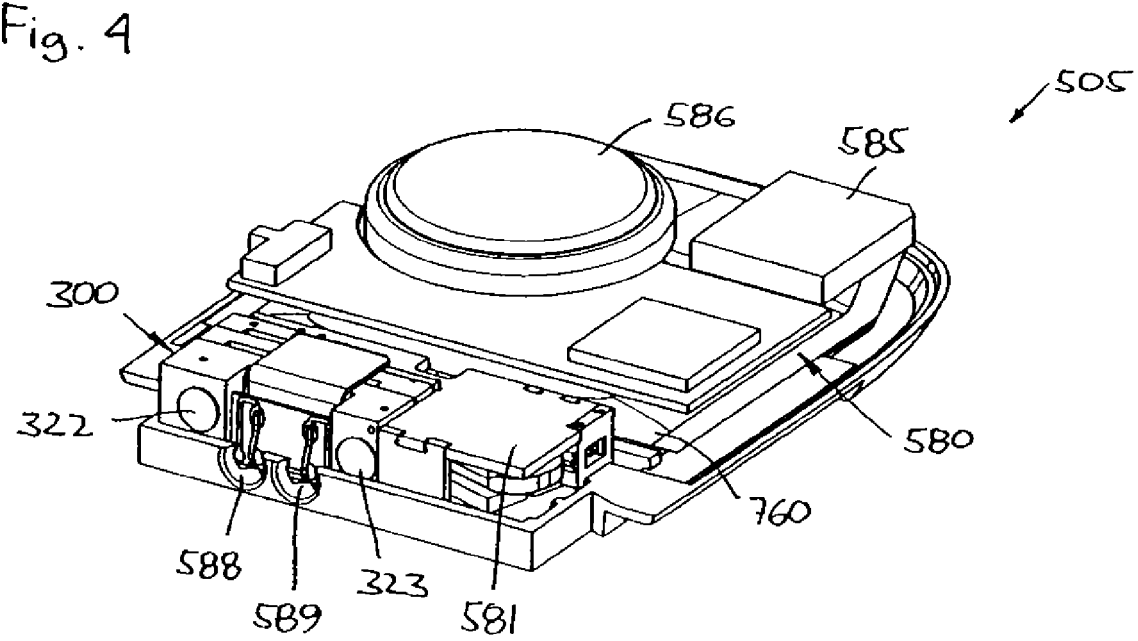
FIG. 4 shows perspective view of the interior of the reservoir unit of FIG. 1.

FIG. 4 shows the pump unit with an upper portion of the housing removed. The pump unit comprises a reservoir 760 and an expelling assembly comprising a pump assembly 300 as well as processor means 580 and a coil actuator 581 for control and actuation thereof. The pump assembly comprises an outlet 322 for connection to a transcutaneous access device and an opening 323 allowing a fluid connector arranged in the pump assembly to be actuated and thereby connect the pump assembly with the reservoir. The reservoir 760 is in the form of prefilled, flexible and collapsible pouch comprising a needle-penetratable septum adapted to be arranged in fluid communication with the pump assembly. The lower portion of the housing comprises a transparent area (not seen) allowing a user to inspect a portion of the reservoir. The shown pump assembly is a mechanically actuated membrane pump, however, the reservoir and expelling means may be of any suitable configuration.

The processor means 580 comprises a PCB or flex-print to which are connected a microprocessor for controlling, among other, the pump actuation, contacts (i.e. sensors) 588, 589 cooperating with corresponding contact actuators on the patch unit or the remote unit (see below), signal generating means 585 for generating an audible and/or tactile signal, a display (if provided), a memory, a transmitter and a receiver. An energy source 586 provides energy. The contacts may be protected by membranes which may be formed by flexible portions of the housing.

With reference to FIGS. 1-4 a modular local unit comprising a pump unit and a patch unit has been described, however, the local unit may also be provided as a unitary unit.

Although the present invention will be described with reference to the pump unit and the remote controller unit disclosed in FIGS. 1-6, it should be understood that the present disclosure is broadly applicable to any form of system comprising a pump unit in combination with a controller unit or other external unit, e.g. a PC or PDA. For example, the present disclosure may be used with programmable ambulatory insulin infusion pumps of the sort currently commercially available from a number of manufacturers, including without limitation and by way of example, Medtronic MiniMed under the trademark PARADIGM, Insulet Corporation under the trademark OmniPod, Smiths Medical under the trademark Deltec COZMO, and others, these pumps either being provided with a remote control or being adaptable to be used with one.

Figure 5:
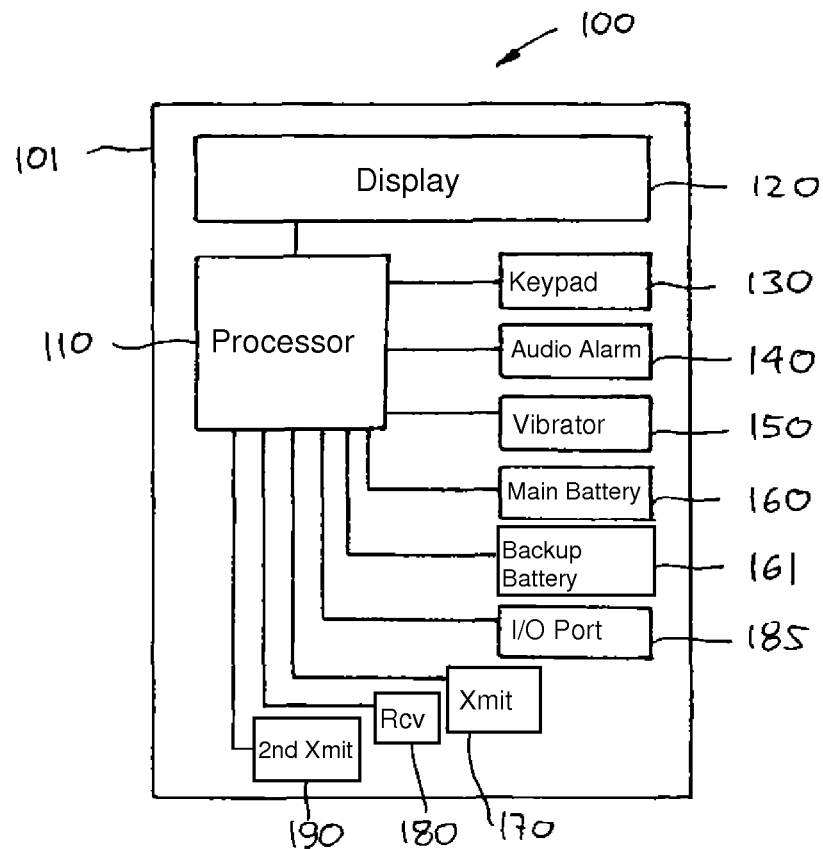
FIG. 5 shows a schematic representation of a process unit and a control unit.
Figure 5:
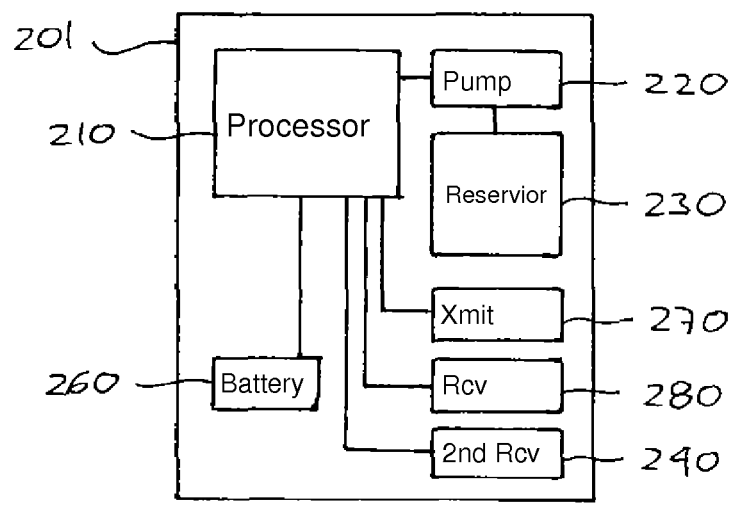

FIG. 5 shows a schematic representation of a process unit 200 (here corresponding to the pump unit 5 of FIG. 1) and a controller unit 100 (here in the form of a wireless "remote controller" or "external communication device" for the pump unit). It is considered that the general design of such units is well known to the skilled person, however, for a more detailed description of the circuitry necessary to provide the desired functionality of the present invention reference is made to incorporated US 2003/0065308.

More specifically, FIG. 5 depicts a simplified block diagram of various functional components or modules (i.e. single components or groups of components) included in the pump unit 200 and remote controller 100. The remote controller unit includes a housing 101, a remote processor 110 including a CPU, memory elements for storing control programs and operation data and a clock, an LCD display 120 for providing operation for information to the user, a keypad 130 for taking input from the user, an audio alarm 140 for providing information to the user, a vibrator 150 for providing information to the user, a main battery 160 for supplying power to the controller, a backup battery 161 to provide memory maintenance for the controller, a remote radio frequency (RF) telemetry transmitter 170 for sending signals to the pump unit, a remote radio frequency (RF) telemetry receiver 180 for receiving signals from the pump unit, and a second transmitter 190. The controller further comprises a port 185, e.g. an infrared (IR) or RF input/output system, or a USB port for communicating with a further device, e.g. a blood glucose meter (BGM), a continuous blood glucose meter (CGM), a PC or a PDA.

As also depicted in FIG. 5, the pump unit 200 includes a housing 201, local processor electronics 210 including a CPU and memory elements for storing control programs and operation data, battery 260 for providing power to the system, a process unit RF telemetry transmitter 270 for sending communication signals to the remote unit, a process unit radio frequency (RF) telemetry receiver 280 for receiving signals from the remote unit, a second process unit receiver 240 (which may be in the form of a coil of an acoustic transducer used in an audio alarm for providing feedback to the user), a reservoir 230 for storing a drug, and a pump assembly 220 for expelling drug from the reservoir through a transcutaneous device to the body of a patient. In alternative embodiments the pump unit may also comprise an LCD display for providing information to the user, a keypad for taking input from the user, and a vibrator or other tactile actuator for providing information to the user. RF transmission may be proprietary or in accordance with a standard protocol such as Bluetooth®.

FIG. 6 shows a schematic representation of a medical system 400 comprising a process unit 420 and a remote controller unit 410 basically corresponding to the units described with reference to FIG. 5. The system comprises first means of communication allowing a first group of data types to be transmitted between the first unit and the second unit, and second means of communication allowing a second group of data types to be transmitted between the first unit and the second unit. The first means of communication is by NFC (Near-Field Communication) having a transmitter coil 411 and a receiver coil 421. Transmission may be by induction using a 125 kHz signal providing a range of approximately 10 cm. The receiver coil may form part of a conventional loudspeaker (see below). The second means of communication is bi-directional using 2.4 GHz RF communication using a pair of antennas 412, 422, this providing a range of communication of several meters.

When a new process unit 420 in the form of a pump is to be paired with a given remote controller 410, the controller is arranged in close proximity to the pump unit and a pairing signal is sent by NFC. The signal comprises a pairing start code, a remote ID and a sequential pump number. When the signal has been received by the pump unit an acknowledgement signal is sent using RF transmission, the acknowledgement comprising the remote ID and the sequential pump number. In this way the two units can only transmit and receive signals intended for the paired pump respectively controller unit. When the remote unit is paired with the next pump unit using the next sequential number, only signals to or from the new pump is transmitted respectively received.

Figure 7A:
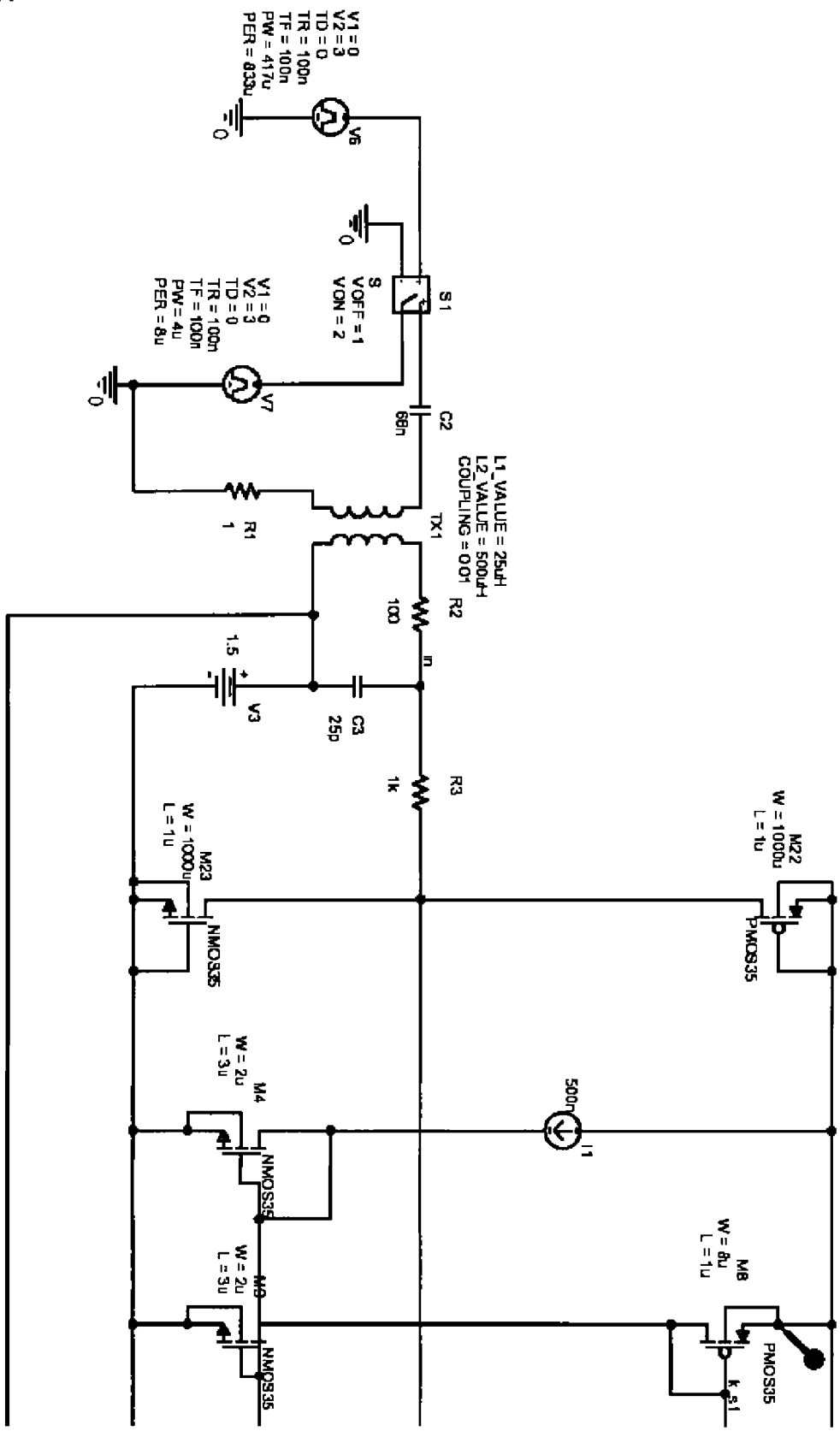
FIGS. 7A-7C show in schematic form a circuitry divided in three images (to be read in directions from A to C), FIGS. 8A-8K (numeral 8(I) not used) show steps of a pairing procedure between two medical units.
Figure 7B:
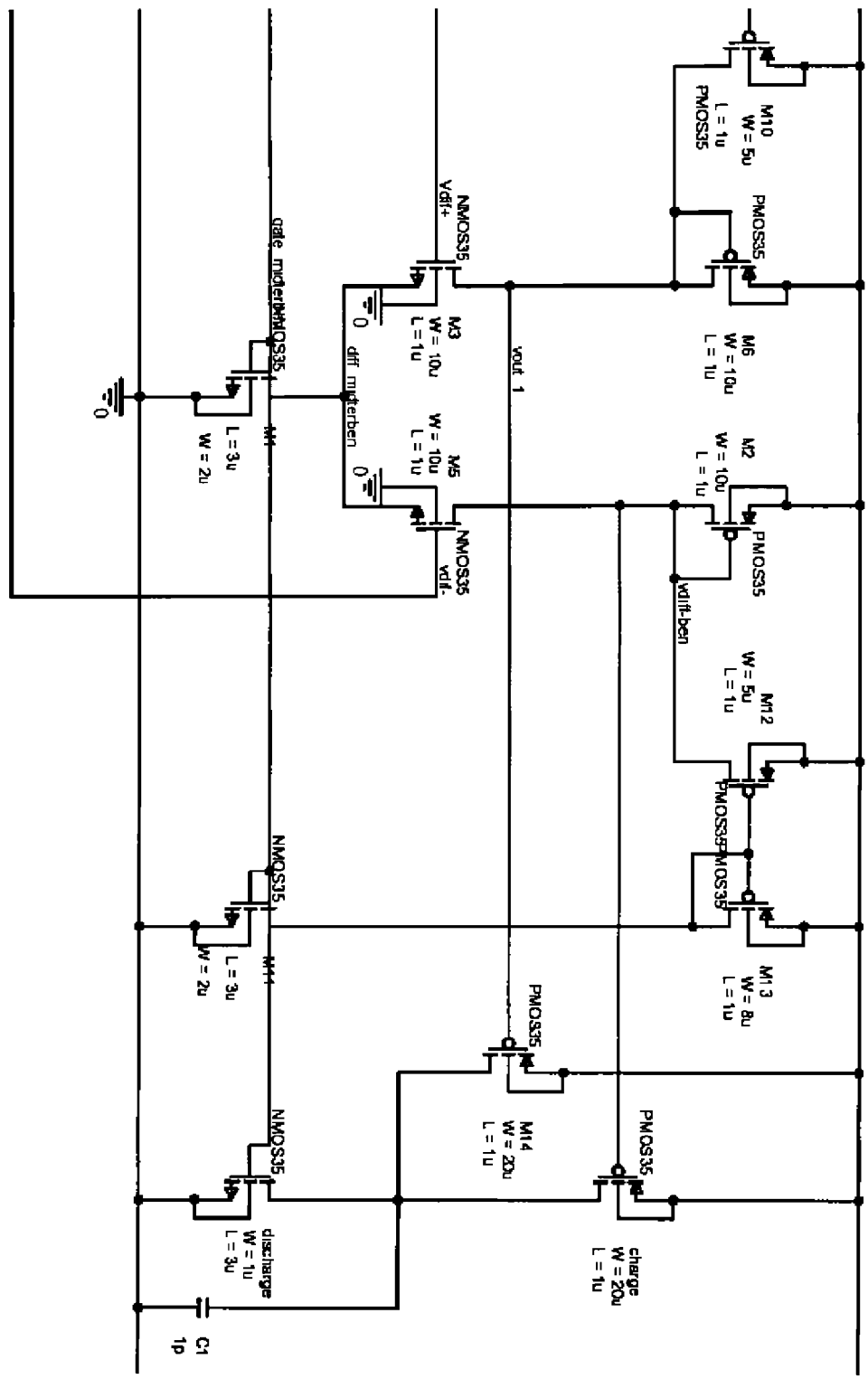
Figure 7C:
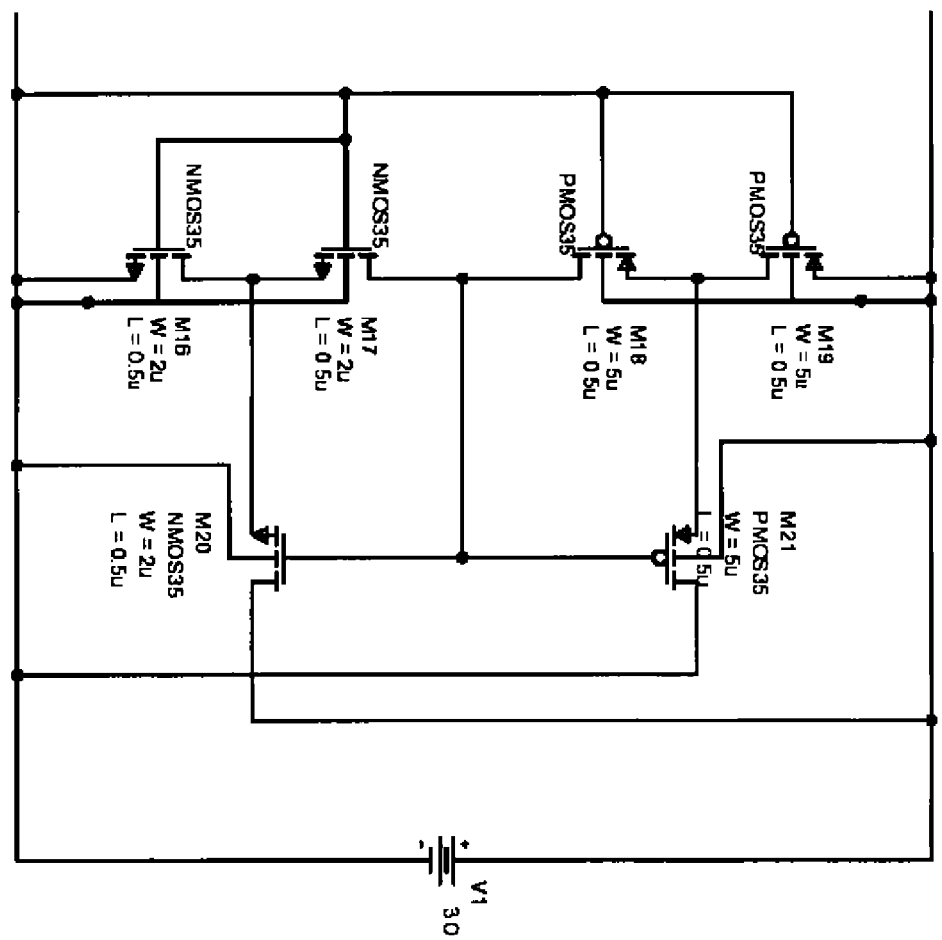

FIG. 7 shows in schematic form circuitry adapted to receive signals generated by induction in a coil (e.g. a loudspeaker coil), the signals being transformed from analog to digital representation which can then be processed by a processor in the pump unit. More specifically, an example of a receiver stage optimized for ASIC-implementation is shown. Amplification and double rectifying of the input signal, from the receiver coil, is performed by the differential stage circuit centred around M3 & M5 seen in the middle. The digitalized signal is noise reduced by the Schmidt-trigger circuit seen on the right of the output voltage signal placed over the capacitance, C1.

Figure 8G:
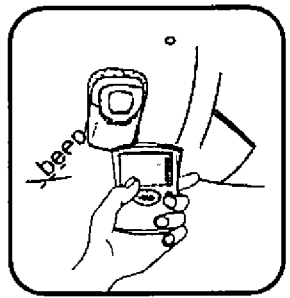
Figure 8C:
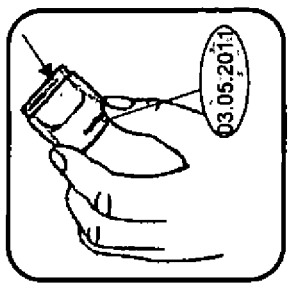
Figure 8F:
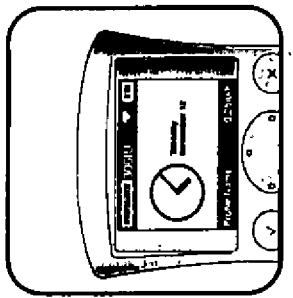
Figure 8K:
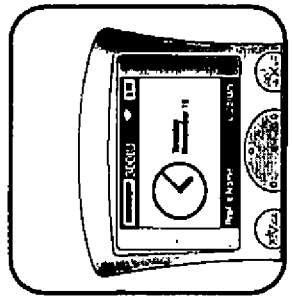
Figure 8B:
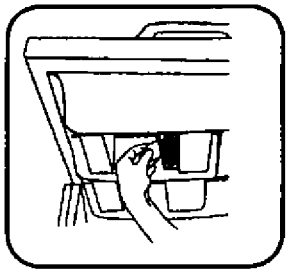
Figure 8E:
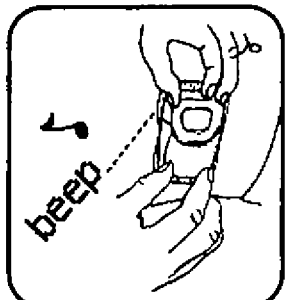
Figure 8J:
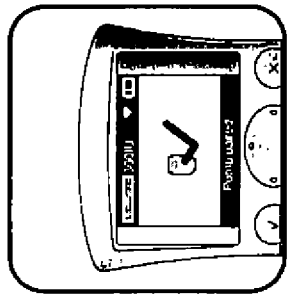
Figure 8A:
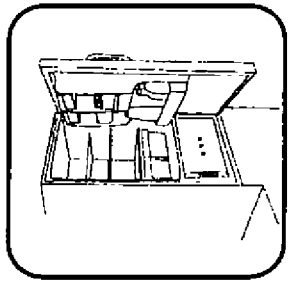
Figure 8D:
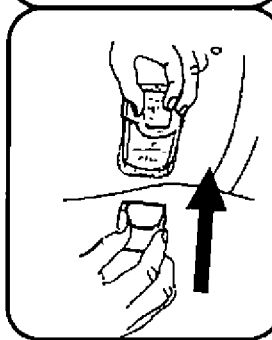
Figure 8H:
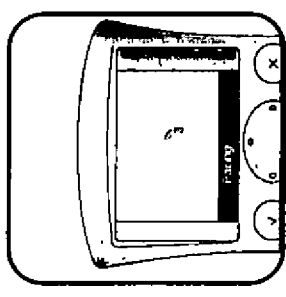

Next two examples of use of a medical drug delivery system implementing embodiments of the present invention will be described. First, a pump unit comprising an insulin formulation is stored in a refrigerator (FIG. 8A). When a new pump unit is taken out from the refrigerator (FIG. 8B), unpacking the pump starts it's electrical life. Before deciding to use the pump unit the expiration date printed on the pump unit is checked by the user (FIG. 8C). A patch unit is mounted on a suitable skin portion of the user. The user then grabs the patch unit and inserts the pump unit by pressing it into the patch unit (FIG. 8D). When assembled, the pump unit is ready for pairing which is indicated by a beep signal (FIG. 8E). Activating the pairing mode allows pairing of the remote (FIG. 8F). Holding the remote close to the pump starts the pairing using NFC, either automatically or by pressing a key. Pump beeps to confirm pairing and pump unit information is transmitted by RF to the remote unit (FIG. 8G). When paired the remote unit displays residual insulin and type, this indicating that the units have been paired and information has been properly received from the pump unit. Depending on the set-up of the system, the remote unit can be paired only with a new unit, or also pairing with a partly used pump unit can be allowed, the latter allowing the user to shift between different pumps and thus types of drug (FIG. 8H). After pressing "Accept" the remote displays "pump paired" and sounds a confirmation beep (FIG. 8J) after which the remote displays e.g. the currently active rate (FIG. 8K).

Next, an example of user authentication using NFC in combination with long-range RF communication will be described.

When in the bolus menu, bolus type and amount is set by the user (FIG. 9A), the user accept the bolus. The display indicates by "safe transmit" that the desired bolus command can only be transmitted using NFC, i.e. by bringing the remote controller into close proximity of the pump unit (FIG. 9B). Next the user swipes the pump with the remote controller to authenticate the bolus command. Transmission may take place either automatically or this may happen either automatically or by pressing a key. The pump beeps to acknowledge reception of the bolus command (FIG. 9C) and transmits an acknowledgement to the remote commander using RF communication, the remote controller showing a checkmark in the display to indicate that the bolus command has been correctly received by the pump unit (FIG. 9D).

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A medical system comprising a first unit and a second unit, the system comprising:
    a first wireless communication link configured to transmit a first group of data types between the first unit and to the second unit, the first group of data types including pairing information for pairing the first unit and second unit, the first unit having a first unit identification number and the second unit being assigned a sequential second unit identification number, the second identification number being assigned by the first unit, and a second wireless communication link configured to transmit a second group of data types between the first unit and the second unit after the first unit and second unit are paired, the second group of data including other information, the first wireless communication link having a shorter range of communication than the second wireless communication link, the first unit having a first processor configured to transmit the pairing information via the first communication link and to transmit or receive the other information via the second communication link, the pairing information including the first unit identification number and the second unit identification number, the second unit having a second processor configured to receive the pairing information via the first communication link and send an acknowledgment via the second communication link, the acknowledgment including the first unit identification number and the second unit identification number, the first and second units then being configured to exchange communications via the second communication link only when the received second unit identification number matches the assigned second unit identification number.

2. A medical system as in claim 1, wherein the first communication link is selected from the group comprising:
RF communication, optical communication and ultrasonic communication, and
wherein the second communication link is selected from the group comprising:
RF communication, ultrasonic communication, and optical communication.

3. A medical system as in claim 1, wherein the first communication link has a range of communication less than 0.5 meter, and the second communication link has a range of communication of more than 0.5 meter.

4. A medical system as in claim 1, wherein the first communication link is an RF communication link at a frequency of less than 24 MHz, and the second communication link is an RF communication link at a frequency of more than 24 MHz.

5. A medical system as in claim 1, wherein at least one of the communication links provides uni-directional communication only between the two units.

6. A medical system as in claim 1, wherein the first communication link provides uni-directional communication from the second unit to the first unit, and the second communication link provides bi-directional communication between the first unit and the second unit.

7. A medical system as in claim 1, wherein the first group of data types comprises a time stamp.

8. A medical system as in claim 1, wherein the first group of data types comprises an activation command, the first unit being configured to allow one or more types of commands from the second group of data types to be received and executed for a given period of time after an activation command has been received.

9. A medical system as in claim 1, wherein the second group of data types comprises a unique ID for the first unit.

10. A medical system as in claim 1, wherein the first unit is a remote controller unit and the second unit is a process unit.

11. A medical system as in claim 10, further comprising an acoustic transducer having a transducer coil with a plurality of windings, the transducer coil serving as a receiver for wireless inductive signals.

12. A medical system as in claim 11, the process unit comprising:
a process unit transmitter,
a process unit receiver, and
a process unit processor connected to the process unit transmitter, the process unit receiver and the transducer coil,
the controller unit comprising:
a first controller unit transmitter configured to transmit information to the transducer coil,
a second controller unit transmitter configured to transmit information to the process unit receiver,
a controller unit receiver configured for receiving information from the process unit transmitter, and
a controller unit processor connected to the first and second controller unit transmitters and the controller unit receiver,
wherein the first communication link comprises the transducer coil and the first controller unit transmitter, and the second communication link comprises the process unit transmitter, the process unit receiver, the second controller unit transmitter, and the controller unit receiver.

13. A medical system as in claim 10, wherein the process unit comprises a reservoir configured to contain a fluid drug, an expelling assembly configured for cooperation with the reservoir to expel fluid drug from the reservoir to a subject via an outlet, and a processor for controlling the expelling assembly.

14. A medical system as in claim 13, wherein the first group of data types comprises at least one type of command controlling the delivery of an amount of fluid drug to the subject.

15. A medical device as in claim 13, wherein the outlet comprises a transcutaneous access device configured to allow a fluid drug to be expelled out of the reservoir and through the skin of the subject via the transcutaneous access device.

16. A medical system as in claim 1, wherein the first unit comprises a processor configured to transmit and/or process data acquired via a sensor device.

17. A medical system as in claim 16, further comprising a transcutaneous sensor device configured for cooperation with the processor.

18. A medical system as in claim 1, further comprising a transcutaneous device unit, the transcutaneous device unit comprising:
a transcutaneous device, and
a mounting surface configured for application to the skin of a subject,
wherein the transcutaneous device unit and the first unit are configured to be secured to each other to form a combined device.

19. A medical system as in claim 1, wherein at least one data type can only be transmitted by one of the first and second communication links.

20. A medical system as in claim 1, wherein at least one data type can be transmitted by both of the first and second communication links.

21. A medical unit, comprising:
a first wireless communication link configured to transmit a first group of data types between the unit and a further unit, the first group of data types including pairing information for pairing the unit and a further unit, the unit having a unit identification number and the further unit being assigned a sequential further unit identification number, the further unit identification number being assigned by the unit, and
a second wireless communication link configured to transmit a second group of data types between the unit and the further unit after the first unit and further unit are paired, the second group of data types including other information, the first wireless communication link having a shorter range of communication than the second wireless communication link, the unit having a first processor configured to transmit the pairing information via the first communication link and to transmit or receive the other information via the second communication link, the pairing information including the unit identification number and the further unit identification number, the further unit having a second processor configured to receive the pairing information via the first communication link and send an acknowledgment via the second communication link, the acknowledgment including the unit identification number and the further unit identification number, the unit and further unit then being configured to exchange communications via the second communication link only when the received further unit identification number matches the assigned further unit identification number.

22. A medical unit as in claim 21, wherein at least one of the communication links provides uni-directional communication only between the unit and the further unit.

23. A method of operating a medical system comprising first and second units, the method comprising:

providing a medical system having first and second units, the first unit having a first unit identification number and the second unit a sequential second unit identification number, the second identification number being assigned by the first unit, transmitting a first group of data types from the first unit to the second unit using a first wireless communication link, the first group of data types including pairing information for pairing the first unit and second unit, the pairing information including the first unit identification number and the second unit identification number, and transmitting a second group of data types between the first unit and the second unit using a second wireless communication link after the first unit and second unit are paired, the second group of data types including other information, the first communication link having a shorter range of communication than the second communication link, and providing a first processor in the first unit, the first processor being configured to transmit the pairing information via the first communication link and to transmit or receive the other information via the second communication link, providing a second processor in the second unit, the second processor being configured receive the pairing information via the first communication link and send an acknowledgment via the second communication link, the acknowledgment including the first unit identification number and the second unit identification number, the first and second units then being configured to exchange communications via the second communication link only when the received second unit identification number matches the assigned second unit identification number.

24. A medical drug delivery system comprising:

a remote controller and a process unit, the remote controller having a remote controller identification number and the process unit being assigned a sequential process unit identification number, the process unit identification number being assigned by the remote controller;

the remote controller being configured with a near field communication (NFC) wireless transmitter and a second wireless receiver, the NFC wireless transmitter being configured to transmit pairing information or a bolus command from the remote controller to the process unit, the pairing information including a pairing start code, the controller unit identification number and the process unit identification number; and the process unit being configured with a NFC wireless receiver and a second wireless transmitter, the NFC wireless receiver being configured to receive the pairing information or bolus command from the remote controller and send an acknowledgment via a second wireless transmitter, the acknowledgment including the remote controller identification number and the process unit identification number, the remote controller being configured to receive communications via the second wireless receiver only when the received process unit identification number matches the assigned process unit identification number, the NFC wireless communication transmitter having a shorter range of communication than the second wireless transmitter.

25. A medical drug delivery system as in claim 24, wherein the second wireless transmitter is selected from the group comprising:

RF communication, ultrasonic communication, and optical communication.

26. A medical drug delivery system as in claim 24, wherein the first NFC wireless transmitter has a range of communication less than 0.5 meter, and the second wireless transmitter has a range of communication of more than 0.5 meter.

* * * * *